(12) United States Patent
Manzke et al.

(10) Patent No.: US 7,436,925 B2
(45) Date of Patent: Oct. 14, 2008

(54) COMPUTER TOMOGRAPHY METHOD FOR OBJECTS MOVING PERIODICALLY

(75) Inventors: Robert Manzke, Husberg (DE); Michael Grass, Buchholz in der Nordheide (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1 day.

(21) Appl. No.: 10/596,150

(22) PCT Filed: Dec. 1, 2004

(86) PCT No.: PCT/IB2004/052612

§ 371 (c)(1),
(2), (4) Date: Jun. 1, 2006

(87) PCT Pub. No.: WO2005/055829

PCT Pub. Date: Jun. 23, 2005

(65) Prior Publication Data

US 2007/0086562 A1 Apr. 19, 2007

(30) Foreign Application Priority Data

Dec. 8, 2003 (EP) ................................ 03104582

(51) Int. Cl.
*A61B 6/03* (2006.01)
(52) U.S. Cl. ........................................................ 378/8
(58) Field of Classification Search .............. 378/8, 378/95, 4, 901, 131; 600/428; 382/131
See application file for complete search history.

(56) References Cited

U.S. PATENT DOCUMENTS

| | | | |
|---|---|---|---|
| 5,383,231 A | 1/1995 | Yamagishi | |
| 5,751,782 A | 5/1998 | Yoshitome | |
| 6,504,894 B2 | 1/2003 | Pan et al. | |
| 6,510,337 B1 | 1/2003 | Heuscher et al. | |
| 6,529,575 B1 * | 3/2003 | Hsieh | 378/4 |
| 6,539,074 B1 | 3/2003 | Yavuz et al. | |

(Continued)

OTHER PUBLICATIONS

Manzke et al., Automatic phase determination for retrospectively gated cardiac CT, Nov. 22, 2004, Med. Phys. 31 (12), pp. 3345-3362.*

(Continued)

*Primary Examiner*—Chih-Cheng G Kao
*Assistant Examiner*—John M Corbett

(57) ABSTRACT

The invention relates to a computer tomography method in which a bundle of rays passes through an object that is moving periodically, in particular a heart. During the acquisition of measured values, a movement signal dependent on the movement of the object is sensed. From this movement signal are determined periodically repeated phases of movement, after which a plurality of intermediate images of a region of the object are reconstructed, in particular at a low resolution, using measured values whose times of acquisition were situated in different phases of movement, thus enabling each intermediate image to be assigned to a phase of movement. The phase of movement in which the object moved least in the region is then identified by determining the intermediate image having the fewest motion artifacts. Finally, a computer tomographic image of the region is reconstructed, in particular with a high spatial resolution, from measured values whose times of acquisition were situated in the phase of movement in which there was the least movement by the object in said region.

20 Claims, 5 Drawing Sheets

U.S. PATENT DOCUMENTS

| | | | |
|---|---|---|---|
| 6,865,248 | B1 | 3/2005 | Rasche et al. |
| 7,277,565 | B2 * | 10/2007 | Rasche et al. ............... 382/128 |
| 2001/0043671 | A1 * | 11/2001 | Grass et al. ................ 378/210 |
| 2003/0007593 | A1 | 1/2003 | Heuscher et al. |
| 2003/0092983 | A1 | 5/2003 | Baker et al. |
| 2004/0062342 | A1 * | 4/2004 | Cahill ........................... 378/4 |
| 2005/0111622 | A1 * | 5/2005 | Bruder et al. ................. 378/95 |
| 2005/0226527 | A1 * | 10/2005 | Weese et al. ............... 382/275 |

OTHER PUBLICATIONS

Manzke, Cardiac Cone Beam CT, Sep. 2004, A dissertation submitted in partial fulfillment of the requirements for the degree Doctor of Philosophy of the University of London, available at http://www.cardiac-ct.net/PhD_Manzke_2004_Final.pdf.*

Manzke et al., Artifact Analysis and Reconstruction Improvement in Helical Cardiac Cone Beam CT, Sep. 2004, IEEE Transactions on Medical Imaging, vol. 23, No. 9, pp. 1150-1164.*

Manzke et al., Automatic phase point determination for cardiac CT imaging, Feb. 16, 2004, Medical Imaging 2004, SPIE vol. 5370, pp. 690-700.*

Hoffmann et al., Noninvasive Coronary Angiography with 16-Detector Row CT: Effect of Heart Rate, available on line Nov. 18, 2004, reference 10.1148/radiol.2341031408, Radiology 2005; 234:86-97.*

Vembar, M., et al.; A dynamic approach to identifying desired physiological phases for cardiac imaging using multislice spiral CT; 2003; Med. Phys.; 30(7)1683-1693.

* cited by examiner

COMPUTER TOMOGRAPHY METHOD FOR OBJECTS MOVING PERIODICALLY

The invention relates to a computer tomography method in which a bundle of rays passes through an object that moves periodically, in particular a heart. The invention also relates to a computer tomograph for carrying out the method and to a computer program for controlling the computer tomograph.

In known methods of the kind specified in the paragraph above, the distribution in space of the absorption or attenuation of the radiation in objects moving periodically is reconstructed from measured values that are acquired with a detector unit. When this is done, the periodic movement of the object means that the measured values convey information from different states of the object, which leads to motion artifacts in the dataset that is reconstructed.

To reduce such motion artifacts, what is done in known methods is for movement signals dependent on the movement of the object, such as an electrocardiogram for example, to be recorded simultaneously during the detection of the transmitted rays. The different successive phases of the movement of the object, which are repeated periodically, can be determined from these movement signals. The measured values that are then used to reconstruct the object are solely ones that were acquired when the object was in the same phase of its movement. What a phase of movement is in this case is generally a range of phases that is repeated in each cycle and in which the times of acquisition of the measured values used for reconstruction are situated. If, for example, the phase of movement that has been selected in the case of a heart is 75% to 85% R-R (R-R=the interval between adjacent R peaks in an electrocardiogram), then the measured values that are used for reconstruction are solely ones whose times of acquisition were situated in this range of phases in each of the individual cycles.

What is disadvantageous in this case is that, due for example to the varying rate of heart-beat, the states of the object in the phases of movement in the different cycles are not really the same. In this way, in a phase of movement of 75% to 85% R-R in a period or cycle, the heart, as an object, assumes states that differ from its states as an object in the same phase of movement in a succeeding period, which produces severe motion artifacts. This effect is all the more pronounced the more the object moves in the given phase of movement. An attempt is therefore made in known methods of heart imaging to determine, with the help of the electrocardiogram, that phase of movement in which the object moves least. This however can only be done to an inadequate degree, because the electrocardiogram does not reproduce the movement of the object with sufficient accuracy.

It is an object of the present invention to specify a computer tomography method, a computer tomograph and a computer program in which the motion artifacts are less pronounced.

This object is achieved in accordance with the invention by a computer tomography method having the following steps:

a) generation by a radiation source of a bundle of rays that passes though an object moving periodically, b) production of a relative movement between the radiation source on the one hand and the object on the other hand, which relative movement comprises rotation about an axis of rotation, c) acquisition, with a detector unit and during the relative movement, of measured values that depend on the intensity in the bundle of rays on the far side of the object, d) sensing of a movement signal dependent on the movement of the object with a movement-sensing means and determination of periodically repeated phases of movement with the help of the movement signal sensed, e) reconstruction of a plurality of intermediate images of a region of the object, each intermediate image being reconstructed with measured values that were acquired while the object was in a different phase of movement, thus enabling a phase of movement to be assigned to each intermediate image, f) determination of the phase of movement in which there was least movement of the object in the region, by determining the intermediate image having the fewest motion artifacts in the region, g) reconstruction of a computer tomographic image of the region from measured values that were acquired while the object was in the phase of movement in which there was least movement of the object in said region, the reconstruction parameters that are used in this case differing from the reconstruction parameters used to reconstruct the intermediate images.

Compared with the known methods mentioned above, what is done in accordance with the invention is for that phase of movement first to be determined in which the object moved least, in the region concerned, during the acquisition. The measured values than are then used for the reconstruction are solely ones whose times of acquisition were situated in those phases of movement, in which case, as has already been mentioned above, the phases of movement are generally ranges of phases. This produces a reduction in motion artifacts as compared with known methods.

The term "periodical movement" is not confined to what is meant by a periodicity in the exact sense, i.e. it is not confined to movements in the course of which states of an object are regularly repeated exactly, i.e. exactly identical states of the object occur at exactly equidistant points in time. A periodical movement in the context of the invention covers in particular movements that are not of mathematical exactness, as is known to be the case with organs of the body that move periodically, such as the heart for example. What is meant is that there is a progression through similar, substantially identical, states of the object at points of time that are generally substantially equidistant.

The term region as used herein may comprise the whole of the object or only part thereof.

The reconstruction of the intermediate images with a low spatial resolution leads to a reduction in computing work and cost when the intermediate images are being reconstructed. The spatial resolution of the intermediate images has to be sufficiently high to enable motion artifacts to be discerned in the intermediate images. No other requirements are normally laid down for the resolution of the intermediate images. In particular, it is not necessary to reconstruct intermediate images of as high a spatial resolution as possible such as are required for diagnostic purposes.

A region of the object that is to be examined (the field of view—FOV) is divided into sub-regions. Then, there is determined for each sub-region the respective phase of movement in which the particular sub-region moved least during the acquisition. What are then used for reconstructing a sub-region in the computer tomographic image (CT image) to be reconstructed in conclusion are solely measured values that were acquired while the object was in a phase of movement in which it moved least in the sub-region concerned. Because the object may move differently in different sub-regions, this results in a further reduction in the motion artifacts.

Determining the intermediate image having the fewest motion artifacts by means of a motion-artifact metric and a motion-artifact value, and in particular by means of a mean of gradients of image values of an intermediate image in the direction of the axis of rotation leads to a further reduction in the motion artifacts.

When known methods are being used, motion artifacts occur to a particularly marked degree at points where regions of the object are reconstructed with measured values whose times of acquisition, although they were situated in the same phase of movement, were situated in different periods. Such regions are referred to as overlap regions. Overlap regions occur especially frequently with objects that move fast relative to the data acquisition process, such as the human heart, because high temporal resolution is needed to reconstruct such objects, which means that ranges of phases of movement that are as narrow as possible have to be used. Because the measured values used are solely ones whose times of acquisition were situated in these ranges of phases of movement then, in order to have a sufficient number of measured values available for the reconstruction, measured values from as many different periods as possible are used to reconstruct the same region of the object. An embodiment described herein allows for this fact by assigning to gradients situated in these overlap regions a greater weight than to gradient that are not situated therein. This gives a further reduction in the motion artifacts.

A computer tomograph for performing the method according to the invention is defined herein.

An embodiment described herein defines a computer program for controlling a computer tomograph.

These and other aspects of the invention are apparent from and will be elucidated with reference to the embodiments described hereinafter.

Figure 1:
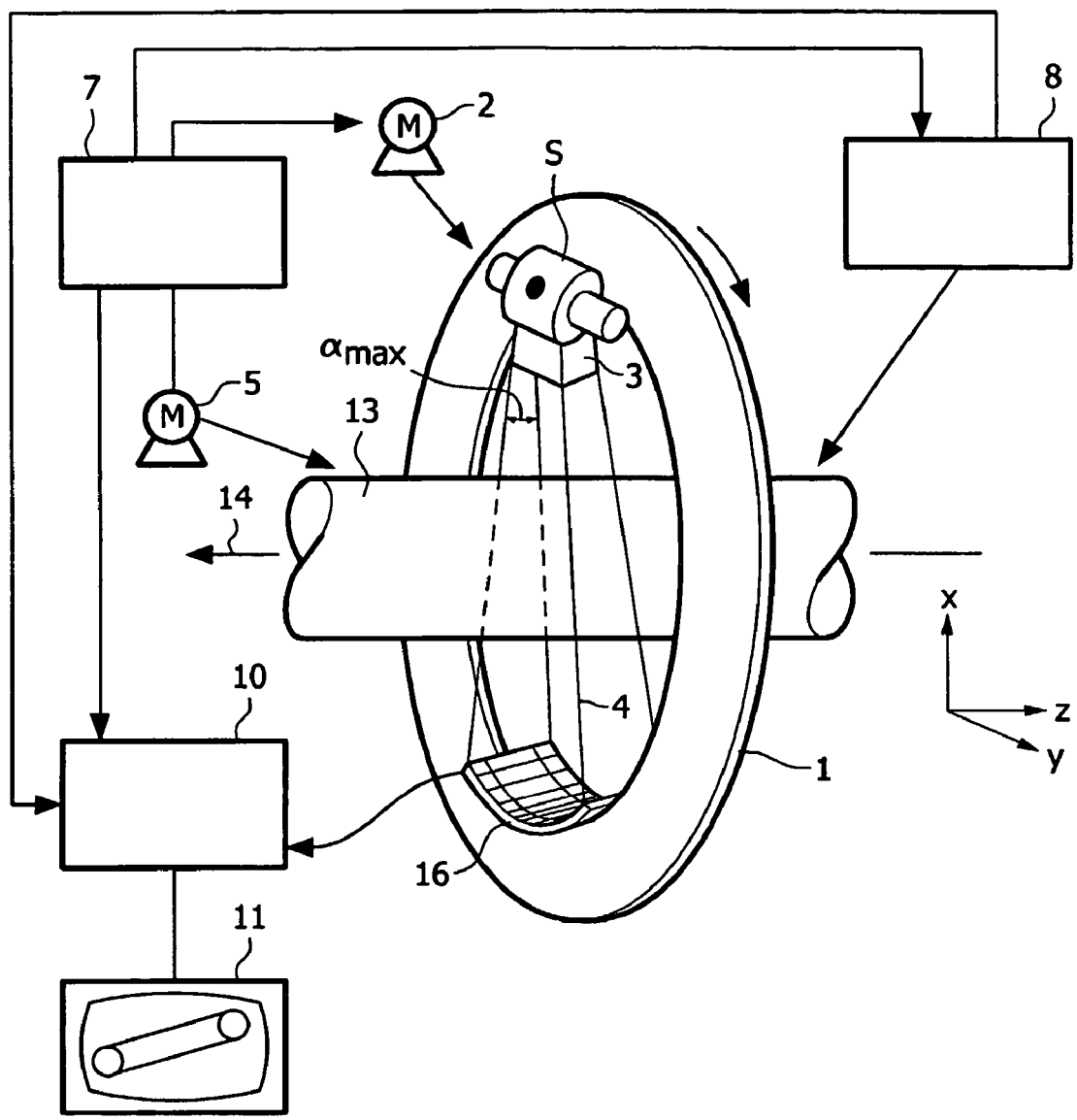
FIG. 1 shows a computer tomograph with which the method according to the invention can be performed.

The computer tomograph shown in FIG. 1 comprises a gantry 1 that is able to rotate about an axis of rotation 14 extending parallel to the z direction of the coordinate system shown in FIG. 1. For this purpose, the gantry 1 is driven by a motor 2 at a preferably constant, settable angular speed. Fastened to the gantry 1 is a radiation source S, preferably an X-ray source. This latter is provided with a collimator arrangement 3 which marks out from the radiation generated by the radiation source S a conical bundle of rays 4, i.e. a bundle of rays that is of a finite extent other than zero both in the z direction and in a direction perpendicular thereto (i.e. in a plane perpendicular to the axis of rotation). As an alternative, a fan-shaped beam could also be used.

The bundle of rays 4 passes through a cylindrical examination region 13 in which is situated an object (not shown) that moves periodically. In the present embodiment, this object is a beating heart that performs spontaneous movements and that may also, under certain circumstances, be moved to and for by respiratory movements of the patient. In other embodiments, the rays might also pass through other parts of the body that move periodically, such as the liver, brain or veins, or though technical objects that move periodically.

Having passed through the examination region 13, the bundle of rays 4 impinges on a detector unit 16 fastened to the gantry 1, which detector unit 16 has a detector surface comprising a plurality of detecting elements that in this embodiment are laid out in rows and columns in the form of a matrix. The columns of detecting elements preferably extend parallel to the axis of rotation 14. The rows of detecting elements are situated in planes perpendicular to the axis of rotation, in the present embodiment along arcs about the radiation source S (making the detector unit a focus-centered detector). In other embodiments however, they may also be differently arranged and may for example describe arcs about the axis of rotation 14 or be in a straight line. Each detector element on which the bundle of rays 4 impinges gives, in each position of the radiation source, a measured value for one ray from the bundle of rays 4. If a fan-shaped bundle of rays is used in other embodiments, then the detector unit could have only a single row of detectors.

The included angle $\alpha_{max}$ of the bundle of rays 4 determines the diameter of the object cylinder within which the object being examined is situated when the measured values are acquired. The included angle is defined in this case as the angle that a ray that is situated at the edge of the bundle of rays 4 in a plane perpendicular to the axis of rotation 14 makes with a plane defined by the radiation source S and the axis of rotation 14. The examination region 13, i.e. the object or the patient presentation table, can be moved by means of a motor 5 parallel to the axis of rotation 14, i.e. to the z axis. As an equivalent to this, it would however also be possible for the gantry to be moved in this direction. When the object involved is a technical one and not a patient, it may be the object that is turned in the course of an examination while the radiation source S and the detector unit 16 remain stationary.

By means of the motors 2 and 5, the radiation source S and the detector unit 16 are able to follow a trajectory relative to the examination region 13 than extends along the surface of an imaginary cylinder. This trajectory may for example be helical in form if both motors operate. If on the other hand the motor 5 for feed in the direction of the axis of rotation 14 remains stopped and the motor 2 causes the gentry to rotate, a circular trajectory will be obtained for the radiation source S and the detector unit 16 relative to the examination region 13. It will be the helical trajectory that is considered in the present embodiment.

During the acquisition of the measured values, the movement of the heart is recorded in a known fashion by means of an electrocardiograph 8. For this purpose, the chest region of a patient is connected to the electrocardiograph 8 via electrodes (not shown). Alternatively, the pulse could also be used as a signal defining the movement of the heart. In other embodiments, and particularly with other moving objects, the movement of the object can be followed with the help of other movement signals. In this way, with a technical object that is moved periodically by a motor, a signal from the motor may be used as a movement signal.

In the present embodiment, it is assumed that the patient does not breathe during the measurement. The respiratory movements can thus be ignored. Alternatively, the respiratory movement could be measured with, for example, a deformable chest belt that was connected to a means of measuring respiratory movement.

The measured values acquired by the detector unit 16 are fed to a reconstructing unit, and particularly a reconstructing computer 10, which is connected to the detector unit 16 by for example a wireless data transmission system (not shown). The electrocardiogram too is transmitted to the reconstructing unit 10, from the electrocardiograph 8. The reconstructing unit 10 reconstructs the distribution of absorption in the examination region 13 and passes it on, to a monitor 11 for example. The two motors 2 and 5, the reconstructing unit 10, the radiation source S, the electrocardiograph 8, the transmission of the measured values from the detector unit 16 to the reconstructing unit 10 and the transmission of the electrocardiogram from the electrocardiograph 8 to the reconstructing unit 10 are controlled by the control unit 7.

In other embodiments, the measured values acquired and the electrocardiograms measured may be fed for reconstruction purposes first to one or more reconstructing computers, which then pass on the reconstructed data to an image-processing computer via, for example, a fiber optic cable.

Figure 2:
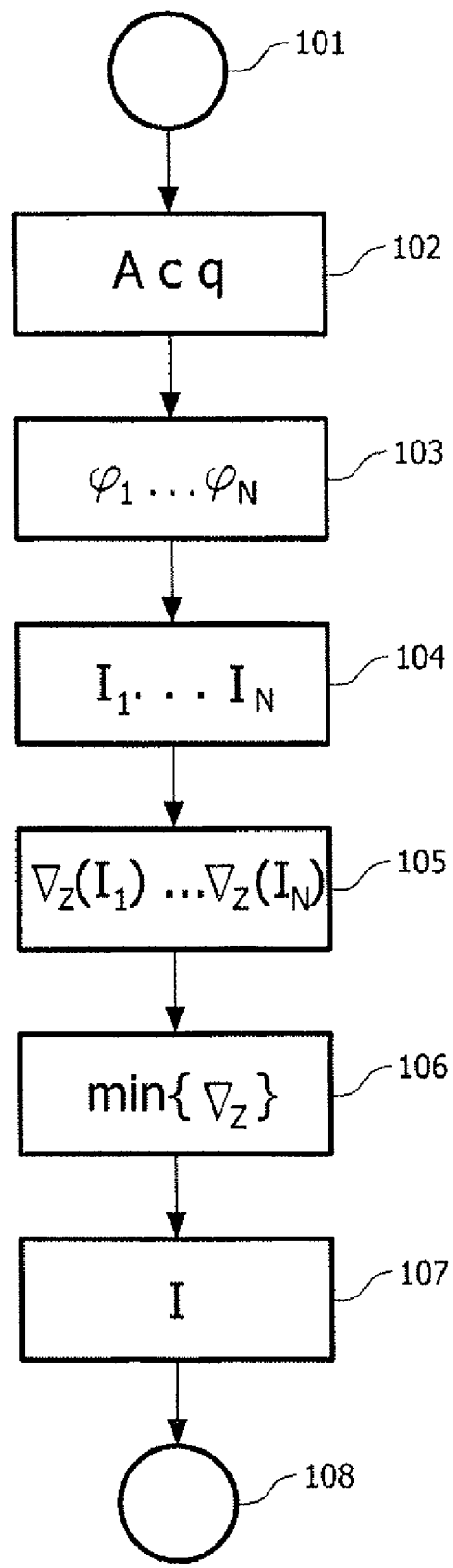
FIG. 2 is a flow-chart of the method according to the invention.

FIG. 2 shows the flow of a measuring and reconstructing method that can be performed with the computer tomograph shown in FIG. 1.

After initialization in step 101, the gantry rotates at an angular speed that is constant in the present embodiment but may also vary, e.g. as a function of time or of the position of the radiation source.

Figure 3:
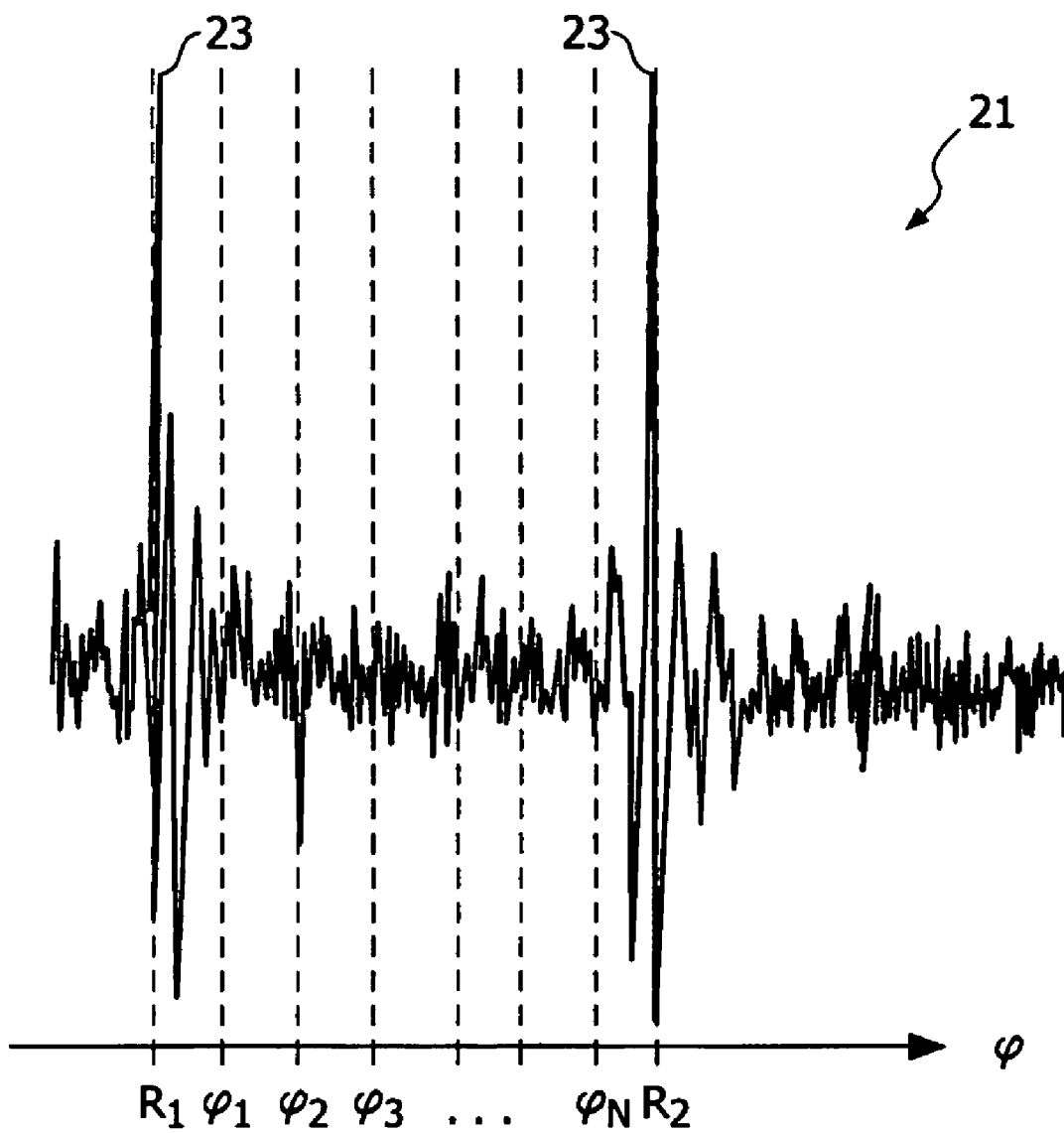
FIG. 3 is a schematic representation of an electrocardiogram, a period, and a plurality of phase points in the period.

In step 102, the examination region, i.e. the object or the patient presentation table, is moved parallel to the axis of rotation and the radiation from the radiation source S is switched on, thus enabling the detector unit 16 to detect the radiation from a plurality of angular positions. As the same time as, or even before, the switching on of the radiation source S, the electrocardiograph 8 is activated, which means that an electrocardiogram 21 (FIG. 3) is measured at the same time.

In step 103, phases of movement, which represent ranges of phases in the present embodiment, are arranged at different phase points $\phi_1 \ldots \phi_N$ within each period with the help of the electrocardiogram 21. For this purpose, one complete period, in which the object passes through each phase of movement once, is defined by the interval between two adjacent R peaks 23 in the electrocardiogram 21. The phase points $\phi_1 \ldots \phi_N$ are then distributed equidistantly for example in each period, e.g. at the points representing 2% R-R, 4% R-R, . . . , 98% R-R. The expression "x % R-R" designates in the present case a point $t=t_R+0.01 \times \Delta t_{R-R}$, where $t_R$ is the time of the first R peak in the period in question and $\Delta T_{R-R}$ is the interval of time between the two R peaks in the period in question. The phases of movement are positioned in each period in such a way that each phase point $\phi_1 \ldots \phi_N$ is in the center of a phase of movement. The width of the phases of movement is determined in the course of step 104.

In step 104, an intermediate image of an object region to be reconstructed (a field of view—FOV) is reconstructed. What this means is that the measured values that are used for reconstructing the intermediate image to be assigned to the phase point $\phi_1$ are solely ones that were acquired while the object was in that phase of movement in the different periods that was located at the phase point $\phi_1$. The same is true of the intermediate images that are assigned to the other phase points. The width of the particular phase of movement is adjusted in this case in such a way that a presettable quantity of measured values are available for reconstructing the particular intermediate image. If for example each voxel of the FOV is to be irradiated over an angular range of at least 180° then, on the basis of the known acquisition geometry, of the angular speed and of the electrocardiogram, appropriate widths have to be determined for the phases of movement by simple geometrical calculations or by computer simulations.

The reconstruction of the intermediate images in step 104 may for example be performed by means of a filtered back-projection, which is explained in detail below in connection with FIG. 4, or by means of known iterative procedures such as ART (algebraic reconstruction technique). Before the reconstruction, each measured value may be weighted by being multiplied by a weighting factor. This weighting factor may be all the larger, the more the corresponding measured value is located in the center of the particular phase of movement.

The reconstruction of the intermediate images is preferably performed with a spatial resolution that is as low as possible (e.g. $20 \times 20 \times 20$ cm$^3$ represented by $32^3$ voxels) but still allows motion artifacts to be detected, the purpose being to minimize computing work and costs.

In step 105, a motion-artifact value is determined for each intermediate image by means of a motion-artifact metric, solely from image values from the particular intermediate image.

It is known that reconstructed CT images of an object that have pronounced motion artifacts have a higher mean gradient of image values in the direction of the axis of rotation 14 (z gradient) than CT images of the same object that have fewer motion artifacts. The mean of the z gradients of image values can therefore be used as a metric for motion artifacts. The smaller this mean is, the fewer motion artifacts there are in the intermediate image in question and the less did the object move in the corresponding phase of movement. A similarity value can therefore be determined by, for example, calculating the z gradient for each voxel of the particular intermediate image and finding the means of the z gradients.

It is also known that a reconstructed CT image of an object that has pronounced motion artifacts has image values that vary greatly with changing angular positions of the radiation source S, whereas in CT images of the same object in which the motion artifacts are less pronounced these changes as a function of the angular position of the radiation source occur to a less marked degree. A mean gradient in the direction of the angle of rotation of the radiation source S can therefore also be used as a motion-artifact metric. A motion-artifact value may for example then be determined by calculating a gradient of the image values in the direction of this angle of rotation for each voxel in the particular intermediate image and finding the mean of these gradients. The resulting mean is then the motion-artifact value for this intermediate image.

When a motion-artifact value is determined with the help of the z gradient, each z gradient may be multiplied by a first weighting factor before the mean is found, a z gradient which is situated in an overlap region of the object being multiplied by a larger first weighting factor than a z gradient that is not situated in an overlap region. An overlap region is a region of the intermediate image that has been reconstructed from measured values whose times of acquisition were situated in different periods. As mentioned at the beginning, motion artifacts occur to a more pronounced degree in these overlap regions, which means that a heavier weighting of the z gradients in the overlap regions will give an additionally improved reduction in the motion artifacts. For example, all the z gradients that are situated in an overlap region may be multiplied by 1 and all the z gradients that are not may be multiplied by 0.

If there are known regions A of the object in which the object has a lower natural z gradient than in other regions B of the object, then a z gradient of the intermediate image that is situated in a region of the image corresponding to a region A of the object, may, in addition, be multiplied, before the mean is found, by a second weighting factor that is larger than a second weighting factor for a z gradient of the intermediate image that is situated in a region of the image corresponding to a region B of the object. In the extreme case, all the z gradients in regions of the image that correspond to region A of the object are multiplied by 1 and all the z gradients in regions of the image that correspond to region B of the object are multiplied by 0. This produces a reduction, by natural z gradients of the object, in the possible disruption of the z gradient caused by motion artifacts and hence to a further reduction of the motion artifacts.

The z gradients may also be multiplied with a combination, and particularly a linear combination, of the first and second weighting factors before the mean is formed. What is more, two motion-artifact values, one obtained with the help of the z gradient and one with the help of the gradient in the direction of the angle of rotation of the radiation source, may be combined, in particular linearly, to give a single motion-artifact value.

In addition to the motion-artifact value, a similarity value can be determined for each intermediate image. For this purpose, each intermediate image is compared with the intermediate images adjacent in time to give a similarity metric. The similarity metric may be any function that gives a value for similarity that is smaller the more similar two intermediate images are. The similarity metric may for example make use of correlations, and particularly the Pearson correlation, and differences in mutually corresponding image values in different intermediate images. A similar value σ for two intermediate images may for example be obtained from the following equation:

$$\sigma = \frac{1}{N} \sum_i |V_{1,i} - V_{2,i}| \text{ where } i = 1, \ldots, N. \quad (1)$$

Here, N is the number of voxels in one of the intermediate images, $V_{1,i}$ is the image value of the ith voxel in a first intermediate image and $V_{2,i}$ is the image value of the ith voxel in a second intermediate image. The mean square deviation of mutually corresponding voxels may also be used as a similarity metric:

$$\sigma = \frac{1}{N} \sum_i \sqrt{(V_{1,i} - V_{2,i})^2} \text{ where } i = 1, \ldots N. \quad (2)$$

Respective similarity values are determined for the first and last intermediate images in time and for all the other intermediate images two similarity values are determined, and in the latter cases a mean is formed of the two similarity values that are assigned to each intermediate image to give one similarity value, so that in the end precisely one similarity value is assigned to each intermediate image.

If the similarity value of an intermediate image is relatively small, then this intermediate image differs to only a small degree from the intermediate images that adjoin it in time, which means that the corresponding object states too are not very different from one another. Hence the object hardly moved in the region of the phase point that is assigned to the intermediate image concerned.

In step 106, an intermediate image is selected that has the lowest motion-artifact value. If, in addition, similarity values were determined in step 105, then for each intermediate image the similarity value can be combined with the motion-artifact value to give a combination value. The combination value may for example be a linear combination, and in particular the mean, of the motion-artifact value and the similarity value. What is then selected in step 106 is an intermediate image that has the lowest combination value.

In step 107 the CT image is reconstructed, the measured values used being solely ones that were situated, in the particular period, in a phase of movement that was located at the phase point that corresponds to the intermediate image determined in step 106. The method according to the invention is not confined in this case to any particular method of reconstruction. The CT image may for example be reconstructed by means of a filtered back-projection that is explained below in connection with FIG. 4, or by means of known iterative methods.

Before the reconstruction, each measured value may be weighted by multiplying it by a weighting factor, if this had not already been done when the corresponding intermediate image was being reconstructed in step 104. This weighting factor may be all the larger, the more the corresponding measured value is positioned in the center of the particular phase of movement.

In contrast to the reconstruction of the intermediate images in step 104, the concluding reconstruction of the object or FOV in step 107 is performed with a high spatial resolution (e.g. 20×20×20 cm³ represented by $512^3$ voxels), in order to obtain an image of the highest possible quality.

Figure 4:
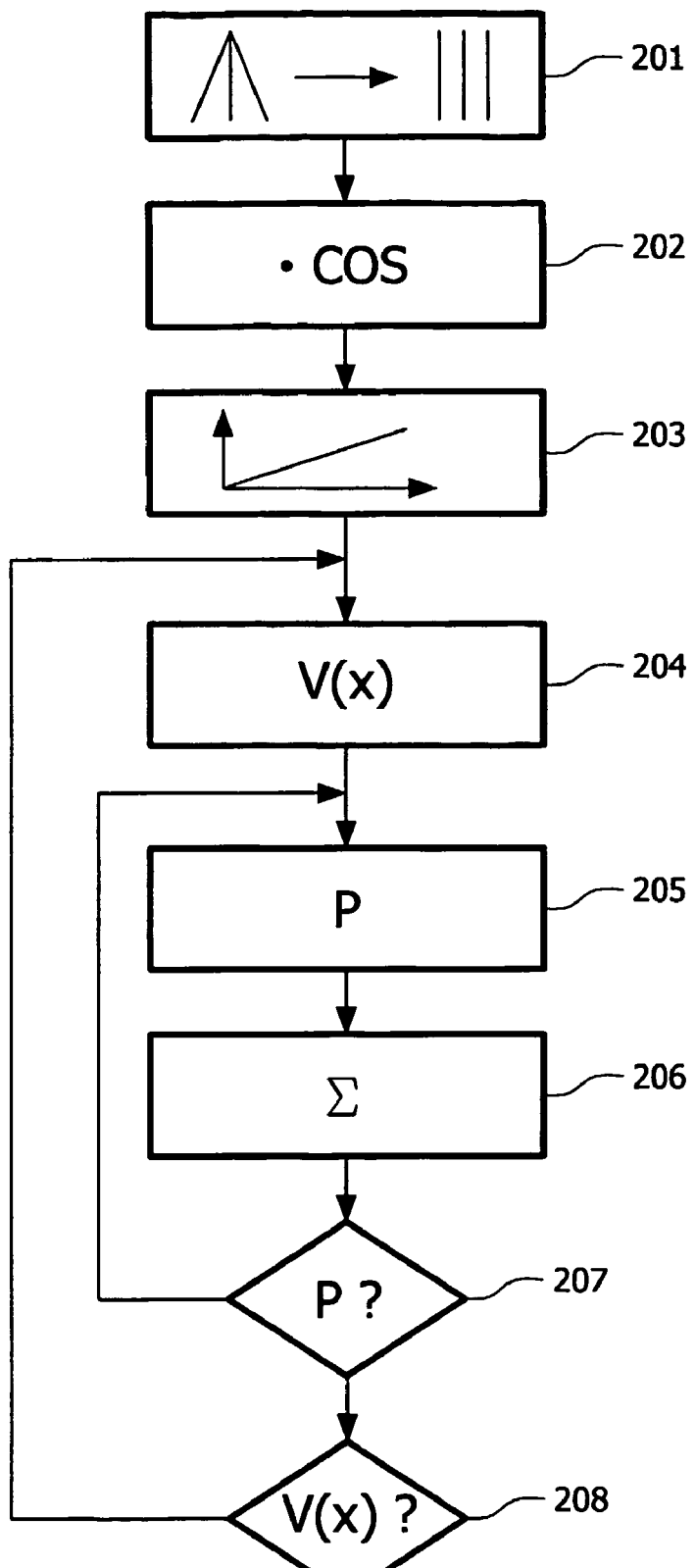
FIG. 4 is a flow chart of a filtered back-projection and FIG. 5 is a schematic perspective view of a helical trajectory, a virtual detector and a plurality of fans of rays.

In what follows, a filtered back-projection by means of which the intermediate images and the concluding CT image can be reconstructed will now be described as an illustrative example (FIG. 4).

For reconstruction, the measured values are regrouped in parallel in step 201. What the parallel regrouping does is resort and re-interpolate the measured values as if they had been measured using a different radiation source (an extended radiation source that is positioned along part of a helix and is able to emit mutually parallel fans of rays in each case) and using a different detector (a plane, rectangular "virtual detector" containing the axis of rotation 14).

Figure 5:
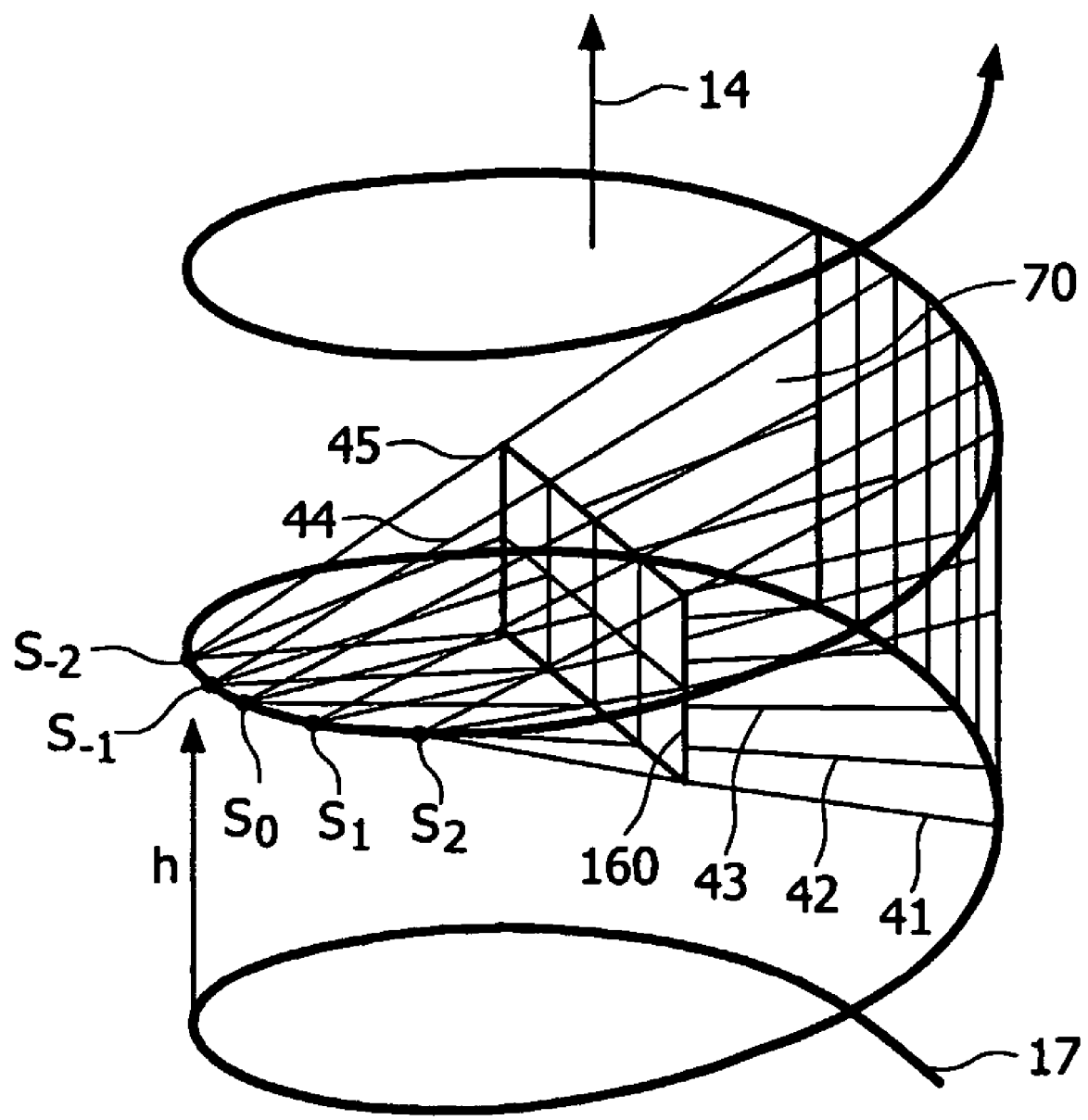

This will be explained in more detail by reference to FIG. 5. Reference numeral 17 in this Figure designates the helical trajectory from which the rays from the radiation source pass through the examination region. A fan-shaped bundle of rays 43, whose rays extend in a plane containing the axis of rotation 14, originates from the radiation source position $S_0$. The conical bundle of rays that is emitted by the radiation source at position $S_0$ can be thought of as composed of a plurality of plane fans of rays that lie in planes parallel to the axis of rotation 14 and intersect at the radiation source position $S_0$. FIG. 5 shows only a single one of these fans of rays, namely fan of rays 43.

Also shown in FIG. 5 are further fans of rays 41, 42 and 44, 45 that are parallel to the fan of rays 43 and lie in planes parallel to one another and to the axis of rotation 14. The associated radiation source positions $S_{-2}$, $S_{-1}$ and $S_1$, $S_2$ are taken up by the radiation source S respectively before and after it reaches radiation source position $S_0$.

The fans of rays 41 to 45 form a group and define a bundle of rays 70 of a tent-like shape. A group of fans of rays is called a projection. For each projection, there is now defined a rectangular virtual detector 160 that lies in a plane that contains the axis of rotation 14 and is oriented perpendicularly to the parallel fans of rays making up a projection. The points forming the corners of the virtual detector 160 are the points at which those rays that, starting from the outer positions of the radiation source, impinge on the section of the helix situated opposite pass through the said plane. For the bundle of rays 70 in FIG. 5, $S_{-2}$ and $S_2$ are the outer radiation source positions. On the rectangular detector 160 are defined detector elements laid out to Cartesian coordinates, i.e. in rows and columns, to which the measured values are re-interpolated.

Then, in step 202, the measured values assigned to the individual rays are multiplied by a weighting factor that is equal to the cosine of the included angle of the individual ray. The included angle of a ray is the angle that this ray makes with a plane that is oriented perpendicularly to the axis of rotation 14. When the said angle is small, its cosine is substantially equal to 1, and step 202 can therefore be dispensed with.

In step 203, one-dimensional filtering with a transmission coefficient that rises in a ramp shape with spatial frequency is applied to the measured values. What are used for this purpose are values that succeed one another in a direction perpendicular to the axis of rotation 14, i.e. along a row of the detector 160. This filtering is performed along each row of the virtual detector for all the groups of fans of rays.

In other embodiments, the parallel regrouping may be dispensed with. It is then known that the filtering has to be modified, because the detector unit is curved, e.g. in an arc, around the radiation source or the axis of rotation.

In step 204, a voxel V(x) is determined within the FOV. Then, in step 205, a projection, i.e. a group of fans of rays, is selected that has not yet been used to reconstruct the voxel V(x) and whose time of acquisition was situated in one of the intervals of time defined above. If there is no ray in the projection that passes through the center of voxel V(x), it is determined at what point a ray that did pass through the center would impinge on the surface of the detector. The associated measured value is then calculated by interpolating from the measured values of adjacent rays. The measured value that can be assigned to that ray of the projection that passes through the voxel, or the corresponding measured value obtained by interpolation, is summed in step 206 to give the voxel V(x). In step 207, a check is made to see whether all the projections have been looked at. If they have not, the flow chart branches back to step 205. Otherwise, a check is made in step 208 as to whether all the voxels V(x) in the FOV have been dealt with. If they have not, the process continues with step 204. If on the other hand all the voxels V(x) in the FOV have been dealt with, then the absorption has been determined in the whole of the FOV and the computer tomography method according to the invention is brought to an end at step 108 (see FIG. 2).

Steps 201 to 203 can be dispensed with when reconstructing the concluding CT image if the measured values have already been treated in the appropriate way when the intermediate images were reconstructed in step 104.

By the method according to the invention, an intermediate image having the lowest motion-artifact value or combination value can be determined for the entire object, i.e. the entire FOV. It is however also possible in accordance with the invention for the FOV to be divided into a plurality of sub-fields (sub-regions of the object), and for an intermediate image having a minimal motion-artifact value or combination value to be determined for each sub-field by steps 104 to 106, thus allowing an optimum phase point to be determined for each sub-field. In the concluding reconstruction in step 107, the measured values used for each sub-field are solely ones that were acquired while the object was in a phase of movement that was situated at the phase point determined for this sub-field. Treating the sub-fields differently in this way allows for the fact that the object may move differently in different ones of its regions, and enable motion artifacts to be further reduced in this way.

LIST OF REFERENCE NUMERALS

| | |
|---|---|
| h | Distance between adjacent turns of a helical trajectory |
| $R_1, R_2$ | Points at which R peaks are situated |
| S | Radiation source |
| $S_{-2} \ldots S_2$ | Radiation source positions |
| $\alpha_{max}$ | Included angle |
| $\phi_1 \ldots \phi_N$ | Phase points |
| 1 | Gantry |
| 2, 5 | Motors |
| 3 | Collimator arrangement |
| 4 | Bundle of rays |
| 7 | Control unit |

-continued

LIST OF REFERENCE NUMERALS

| | |
|---|---|
| 8 | Electrocardiograph |
| 10 | Reconstructing unit |
| 11 | Monitor |
| 13 | Examination region |
| 14 | Axis of rotation |
| 16 | Detector unit |
| 17 | Helical trajectory |
| 21 | Electrocardiogram |
| 23 | R peak |
| 41 … 45 | Fans of rays |
| 70 | Bundle of rays |
| 160 | Virtual detector |

The invention claimed is:

1. A computer tomography method having the following steps:
   a) generating by a radiation source a bundle of rays that passes though an object moving periodically,
   b) producing a relative movement between the radiation source on the one hand and the object on the other hand, which relative movement comprises rotation about an axis of rotation,
   c) acquiring, with a detector unit and during the relative movement, of-measured values that depend on the intensity in the bundle of rays on a far side of the object,
   d) sensing a movement signal dependent on the movement of the object with a movement-sensing means and determining cyclically repeated phases of movement based on the movement signal sensed,
   e) reconstructing reconstruction of a plurality of intermediate images of a region of an object, each intermediate image being reconstructed with measured values that were acquired while the object was in a different phase of movement, and assigning a phase of movement to each intermediate image,
   f) determining the phase of movement in which there was least movement of the object in the region, by determining the intermediate image having the fewest motion artifacts in the region,
   g) reconstructing a computer tomographic image of the region from measured values that were acquired while the object was in the phase of movement in which there was least movement of the object in said region, the reconstruction parameters differing from the reconstructions parameters used to reconstruct the intermediate images.

2. A computer tomography method as claimed in claim 1, wherein the intermediate images in step e) are reconstructed with a lower spatial resolution than the computer tomographic image to be reconstructed in step g).

3. A computer tomography method as claimed in claim 1, wherein the region of the object that is to be analyzed is divided into a plurality of sub-region sand in that steps e) to g) are performed for each sub-region.

4. A computer tomography method as claimed in claim 1, wherein, based on a motion-artifact metric, there is determined for each intermediate image a motion-artifact value by applying the motion-artifact metric solely to measured values from the particular intermediate image, and in that the intermediate image having the lowest motion-artifact value is determined to be the intermediate image having the fewest motion artifacts.

5. A computer tomography method as claimed in claim 4, wherein the motion-artifact value of an intermediate image is the mean of gradients of image values in the intermediate image in the direction of an axis of rotation.

6. A computer tomography method as claimed in claim 5, wherein the gradients are weighted before a mean thereof is formed, wherein a gradient that is situated in an overlap region of the object, through which region rays having acquisition times situated in different periods pass, is given a higher weight than a gradient that is not situated in an overlap region.

7. A computer tomography, having
  a radiation source for generating a bundle of rays that passes through an object moving in a cycle,
  a drive arrangement for producing a relative movement between the radiation source on the one band and the object on the other hand, which relative movement comprises a rotation about an axis of rotation,
  a detector unit for acquiring, during the relative movement, measured values that depend on the intensity in the bundle of rays on the far side of the object,
  a movement-sensing means for the sensing of a movement signal dependent on the movement of the object with a movement-sensing means wherein the movement-sensing means includes an electrocardiograph
  a reconstructing unit for reconstructing a computer tomographic image of the object from the measured values,
  a control unit for controlling the radiation source, the drive arrangement, the detector unit, the movement-sensing means and the reconstructing unit in the following steps:
  a) generating by the radiation source of a bundle of rays that passes though an object that moves periodically,
  b) producing a relative movement between the radiation source on the one hand and the object on the other hand, which relative movement comprises rotation about an axis of rotation,
  c) acquiring with the detector unit and during the relative movement, of measured values that depend on the intensity in the bundle of rays on a far side of the object,
  d) sensing a movement signal dependent on the movement of the object with the movement-sensing means and determining periodically repeated phases of movement based on the movement signal sensed,
  e) reconstructing of a plurality of intermediate images of a region of the object, each intermediate image being reconstructed with measured values that were acquired while the object was in a different phase of movement, a phase of movement to each intermediate image,
  f) determining of the phase of movement in which there was least movement of the object in the region, by determining the intermediate image having the fewest motion artifacts in the region,
  g) reconstructing of a computer tomographic image of the region of the object from measured values that were acquired while the object was in the phase of movement in which there was least movement of the object in said region, the reconstruction parameters that are used in this case differing from the reconstruction parameters used to reconstruct the intermediate images.

8. The computer tomography of claim 7, wherein the reconstructing unit determines a motion-artifact metric for the intermediate images.

9. The computer tomography of claim 7, wherein the reconstructing unit determines a motion-artifact value for the intermediate images.

10. The computer tomography of claim 7, wherein the reconstructing unit determines mean gradients of the intermediate images.

11. The computer tomography of claim 10, wherein the reconstructing unit using the mean gradients to determine the intermediate image that has the fewest motion artifacts.

12. The computer tomography of claim 7, wherein a relatively higher mean gradient is indicative of relatively increased motion artifact.

13. The computer tomography of claim 7, wherein the reconstructing unit determines the mean gradients of image values along the direction of the axis of rotation.

14. The computer tomography of claim 13, wherein the mean gradient is used as a motion-artifact metric.

15. The computer tomography of claim 7, wherein the reconstructing unit determines the mean gradients along the direction of the angle of rotation of the radiation source.

16. The computer tomography of claim 15, wherein the mean gradient is used as a motion-artifact value.

17. The computer tomography of claim 15, wherein the reconstructing unit determines the mean gradient by calculating a gradient of the image values for each voxel in an intermediate image and calculating the mean of these gradients.

18. The computer tomography of claim 15, wherein the reconstructing unit determines the mean gradient by determining gradients of image values along the direction of the angle of rotation of the source, weighting the gradients, and determining the mean of the weighted gradients.

19. A computer readable medium encoded with a computer program for a control unit for controlling a radiation source, a drive arrangement, a detector unit, and a reconstructing unit of a computer tomography for carrying out the steps of:
  generating by the radiation source of a bundle of rays that passes though an object that moves periodically, producing a relative movement between the radiation source on the one hand and the object on the other hand, which relative movement comprises rotation about an axis of rotation,
  acquiring with the detector unit and during the relative movement of measured values that depend on the intensity in the bundle of rays on a far side of the object,
  sensing a movement signal dependent on the movement of the object with the movement-sensing means and determining periodically repeated phases of movement based on the movement signal sensed
  reconstructin a plurality of intermediate images of a region of the object each intermediate image being reconstructed with measured values that were acquired while the object was in a different phase of movement, and assigning a phase of movement to each intermediate image.
  determining the phase of movement in which there was least movement of the object in the region, by determining the intermediate image having the fewest motion artifacts in the region, and
  reconstructing a computer tomographic image of the region of the object from measured values that were acquired while the object was in the phase of movement in which there was least movement of the object in said region the reconstruction parameters differing from the reconstruction parameters used to reconstruct the intermediate images.

20. The computer readable medium of claim 19, wherein the computer program controls the reconstructing unit to carry out the step of determining for each intermediate image a motion-artifact value based on a motion-artifact metric, wherein the intermediate image having the lowest motion-artifact value is determined to be the intermediate image having the fewest motion artifacts.

* * * * *